United States Patent
Makioka et al.

(10) Patent No.: US 6,949,621 B2
(45) Date of Patent: Sep. 27, 2005

(54) POLYMER CONTAINING 9-OXO-9-PHOSPHAFLUORENE-2,7-DIYL SKELETON IN BACKBONE AND PROCESS FOR PRODUCING THE SAME

(75) Inventors: Yoshikazu Makioka, Ibaraki (JP); Masato Tanaka, Ibaraki (JP); Teruyuki Hayashi, Chiba (JP)

(73) Assignees: Japan Science and Technology Corporation, Saitama (JP); National Institute of Advanced Industrial Science and Technology, Tokyo (JP)

( * ) Notice: Subject to any disclaimer, the term of this patent is extended or adjusted under 35 U.S.C. 154(b) by 268 days.

(21) Appl. No.: 10/399,234

(22) PCT Filed: Feb. 27, 2002

(86) PCT No.: PCT/JP02/01774
§ 371 (c)(1),
(2), (4) Date: Apr. 14, 2003

(87) PCT Pub. No.: WO02/072661
PCT Pub. Date: Sep. 19, 2002

(65) Prior Publication Data
US 2004/0019180 A1 Jan. 29, 2004

(30) Foreign Application Priority Data

| Mar. 8, 2001 | (JP) | 2001-064202 |
| Oct. 5, 2001 | (JP) | 2001-310029 |
| Oct. 5, 2001 | (JP) | 2001-310030 |
| Oct. 5, 2001 | (JP) | 2001-310031 |

(51) Int. Cl.$^7$ .................. C08G 79/02; C08G 79/04
(52) U.S. Cl. .................. 528/398; 528/394; 528/397; 528/425
(58) Field of Search .................. 528/398, 394, 528/397, 425

(56) References Cited

FOREIGN PATENT DOCUMENTS

JP  2000-252065 A1  9/2000

OTHER PUBLICATIONS

International Search Report (English Translation).
International Examination Report.
English Translation of the International Preliminary Examination Report dated Oct. 9, 2003.

*Primary Examiner*—Duc Truong
(74) *Attorney, Agent, or Firm*—Rader, Fishman & Grauer PLLC

(57) ABSTRACT

A polymer containing in the backbone a 9-oxo-9-phosphafluorene-2,7-diyl skeleton or a combination of the skeleton with a vinylene skeleton or arylene skeleton. The polymer is utilizable as, e.g., a component of a luminescent element or electrochromic element.

The polymer is obtained by subjecting a 2,7-dihalo-9-oxo-9-phosphafluorene to polycondensation with dehalogenation, or to reaction with arylenebisboronic acid and polycondensation, or to polycondensation with an olefin.

36 Claims, No Drawings

POLYMER CONTAINING 9-OXO-9-PHOSPHAFLUORENE-2,7-DIYL SKELETON IN BACKBONE AND PROCESS FOR PRODUCING THE SAME

TECHNICAL FIELD

The present invention relates to a polymer containing in the backbone a 9-oxo-9-phosphafluorene-2,7-diyl skeleton that is condensed with a phosphorus atom. Precisely, the invention relates to such a polymer that contains in the backbone the skeleton or a combination of the skeleton and a vinylene or arylene skeleton, and to a process for producing the polymer, as well as to use of the polymer for a component of a luminescent element or electrochromic element.

BACKGROUND ART

Methods of producing 9-oxo-9-phosphafluorene-based chemicals are known in the art. However, a polymer that contains in the backbone a 9-oxo-9-phosphafluorene-2,7-diyl skeleton or a combination of the skeleton and a vinylene or arylene skeleton, and a process for producing it, as well as the behavior of the polymer for a component of a luminescent element or electrochromic element are unknown. In addition, 2,7-dihalo-9-alkyl-9-oxo-9-phosphafluorene compounds that are used as the starting monomer for the polymer, and a process for producing them are also unknown.

DISCLOSURE OF THE INVENTION

One object of the present invention is to provide a polymer that contains in the backbone a 9-oxo-9-phosphafluorene-2,7-diyl skeleton or a combination of the skeleton and a vinylene or arylene skeleton, and to provide a process for producing the polymer. The polymer is utilizable as, for example, a component of a luminescent element or electrochromic element. Another object of the invention is to provide a 2,7-dihalo-9-alkyl-9-oxo-9-phosphafluorene compound which is used as the starting monomer for the polymer, and a process for producing the compound.

BEST MODES OF CARRYING OUT THE INVENTION

The invention relates to a polymer that contains in the backbone a 9-oxo-9-phosphafluorene-2,7-diyl skeleton or a combination of the skeleton and a vinylene or arylene skeleton of the following general formula [I], to a process for producing the polymer, and to a luminescent element or an electrochromic element that contain the polymer.

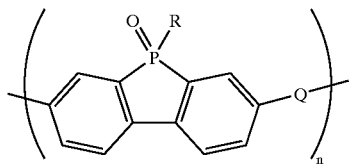

[wherein -Q- represents a single bond, —Ar— (Ar is an arylene group), or a vinylene group of the following general formula [II]:

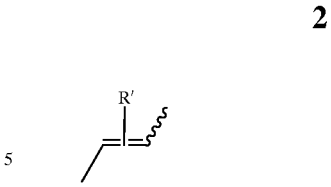

(in which R' represents a hydrogen atom, an optionally-substituted alkyl, cycloalkyl, aryl or aralkyl group, a cyano group, or an alkoxycarbonyl group, and it may bond to any carbon of the olefin chain in the formula);

R represents a hydrogen atom, or an optionally-substituted alkyl, cycloalkyl, aralkyl, aryl, alkoxy, cycloalkyloxy, aralkyloxy or aryloxy group; and n indicates an integer of from 3 to 30000].

Formula [I] where -Q- is a single bond represents a polymer that contains in the backbone a 9-oxo-9-phosphafluorene-2,7-diyl skeleton of the following general formula [III]:

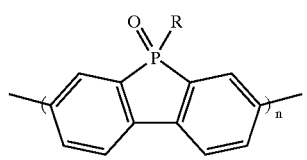

(wherein R and n have the same meanings as above).

Formula [I] where -Q- is —Ar— represents a polymer that contains in the backbone a 9-oxo-9-phosphafluorene-2,7-diyl skeleton and an arylene skeleton of the following general formula [IV]:

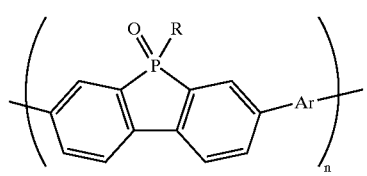

(wherein Ar and n have the same meanings as above).

Formula [I] where -Q- is a vinylene group of formula [II] represents a polymer that contains in the backbone a 9-oxo-9-phosphafluorene-2,7-diyl skeleton and a vinylene skeleton of the following general formula [V]:

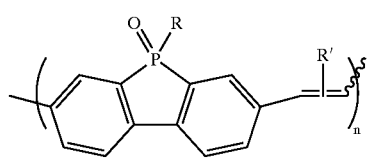

(wherein R, R' and n have the same meanings as above).

In formulae [I], [III], [IV] and [V], R represents a hydrogen atom, or an optionally-substituted alkyl, cycloalkyl, aralkyl, aryl, alkoxy, cycloalkyloxy, aralkyloxy or aryloxy group.

The alkyl group of the optionally-substituted alkyl group for R may be a linear or branched alkyl group preferably having from 1 to 20, more preferably from 1 to 15 carbon atoms. Its examples are methyl, ethyl, n- or iso-propyl, n-, iso- sec- or tert-butyl, n-, iso-, sec-, tert- or neo-pentyl, n-hexyl, n-heptyl, n-octyl, 2-octyl and n-nonyl groups.

The cycloalkyl group of the optionally-substituted cycloalkyl group for R preferably has from 5 to 18, more preferably from 5 to 10 carbon atoms. Its examples are cyclopentyl, cyclohexyl, cyclooctyl and cyclododecyl groups.

The aralkyl group of the optionally-substituted aralkyl group for R preferably has from 7 to 13, more preferably from 7 to 11 carbon atoms. Its examples are benzyl, phenethyl and naphthylmethyl groups.

The aryl group of the optionally-substituted aryl group for R preferably has from 6 to 18, more preferably from 6 to 14 carbon atoms. Its examples are phenyl, naphthyl, tolyl and xylyl groups.

The alkoxy group of the optionally-substituted alkoxy group for R preferably has from 1 to 20, more preferably from 1 to 15 carbon atoms. Its examples are methoxy, ethoxy, n- or iso-propoxy, n-, iso-, sec- or tert-butoxy, n-, iso-, sec-, tert- or neo-pentyloxy, n-hexyloxy, n-heptyloxy, n-octyloxy and 2-octyloxy groups.

The cycloalkyloxy group of the optionally-substituted cycloalkyloxy group for R preferably has from 5 to 18, more preferably from 5 to 10 carbon atoms. Its examples are cyclopentyloxy, cyclohexyloxy, cyclooctyloxy and cyclododecyloxy groups.

The aralkyloxy group of the optionally-substituted aralkyloxy group for R preferably has from 7 to 13, more preferably from 7 to 11 carbon atoms. Its examples are benzyloxy, phenethyloxy and naphthylmethyloxy groups.

The aryloxy group of the optionally-substituted aryloxy group for R preferably has from 6 to 18, more preferably from 6 to 14 carbon atoms. Its examples are phenoxy, 1- or 2-naphthyloxy, tolyloxy and xylyloxy groups.

The substituent for these alkyl, cycloalkyl, aralkyl, aryl, alkoxy, cycloalkyloxy, aralkyloxy and aryloxy groups includes, for example, an alkyl group such as methyl, ethyl, n- or iso-propyl; an alkoxy group such as methoxy, ethoxy; and a halogen atom such as fluorine, chlorine, bromine, iodine. Except these, any other substituent not interfering with the polycondensation in the process of producing the polymer of the invention is acceptable for these groups.

In formula [IV], Ar represents a substituted or unsubstituted arylene group, of which the arylene group has from 6 to 14 carbon atoms. Concretely, it includes 1,4-phenylene, 2-methyl-1,4-phenylene, 2,5-dimethyl-1,4-phenylene, 2,3-dimethyl-1,4-phenylene, 2,3,5,6-tetramethyl-1,4-phenylene, 2,5-dimethoxy-1,4-phenylene, 2,5-dihexyloxy-1,4-phenylene and 2,5-bis(1-methylheptyloxy)-1,4-phenylene groups.

In formulae [II] and [V], R' is a hydrogen atom, an optionally-substituted alkyl, cycloalkyl, aryl or aralkyl group, a cyano group, or an alkoxycarbonyl group.

For the definitions and the examples of the alkyl, cycloalkyl, aryl or aralkyl group of the optionally-substituted alkyl, cycloalkyl, aryl or aralkyl for R', and also for the definitions and the examples of the substituents for these groups, referred to are the same as those mentioned hereinabove for R respectively.

The alkoxycarbonyl group for R' is preferably one containing an alkoxy group having from 1 to 20, more preferably from 1 to 15 carbon atoms. Its examples are methoxycarbonyl, ethoxycarbonyl, n- or iso-propoxycarbonyl, n-, iso-, sec- or tert-butoxycarbonyl, n-, iso-, sec-, tert- or neo-pentoxycarbonyl, n-hexoxycarbonyl, n-heptoxycarbonyl, n-octoxycarbonyl and 2-octoxycarbonyl groups.

R' may bond to any carbon of the olefin site of the formula.

The polymer of formula [III] may be produced through dehalo-polycondensation of a 2,7-dihalo-9-oxo-9-phosphafluorene of the following general formula [VI]:

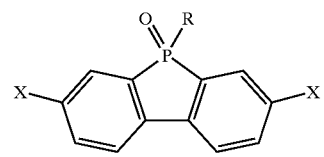

[VI]

(wherein R has the same meaning as above, and X represents a halogen atom).

Examples of the halogen atom for X in formula [VI] are chlorine, bromine and iodine atoms.

The polycondensation effectively goes on in the presence of a transition metal-based chemical substance, especially a low-valance transition metal-based chemical substance that is active to organic halogen compounds in a reaction mode generally known as oxidative addition reaction. The transition metal is preferably a latter-period transition metal of Groups 8 to 10 of the Periodic Table. Concretely, it includes, for example, iron, ruthenium, cobalt, rhodium, iridium, nickel, palladium and platinum. Especially preferred is nickel. The low-valence transition metal-based chemical substance may be previously prepared, or may be prepared in situ by adding a reducing agent to a higher-valence transition metal-based chemical substance and may be directly used in the reaction as it is. The reducing agent includes, for example, sodium borohydride, lithiumaluminium hydride, metal zinc, and hydrazine. Preferably, the amount of the transition metal-based chemical substance to be used is at least 1 equivalent to the 2,7-dihalo-9-oxo-9-phosphafluorene. However, when the reaction is effected in the presence of such a reducing agent, using even a catalytic amount of the compound may attain the intended object.

The polycondensation may be effected at various temperatures, but is generally effected at a temperature falling between −70 and 180° C., preferably between 0 and 150° C.

Preferably, the polycondensation is effected in a solvent. The solvent includes, for example, N,N-dimethylformamide, hexamethylphosphoryl triamide, toluene, benzene, and tetrahydrofuran. The amount of the solvent to be used in effecting the polycondensation is not specifically defined but falls generally between 0.1 and 100 mL, preferably between 1 and 20 mL relative to 1 mmol of the starting 2,7-dihalo-9-oxo-9-phosphafluorene.

After the reaction, the reaction mixture may be post-treated through per-se known extrusion crystallization, filtration or washing with water, and the reaction product may be readily isolated and purified through reprecipitation or the like.

The polymer of formula [IV] may be produced by dissolving the 2,7-dihalo-9-oxo-9-phosphafluorene of formula [VI] in a solvent followed by polycondensing it with an arylenebisboronic acid of the following general formula [VII]:

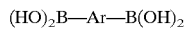

(HO)$_2$B—Ar—B(OH)$_2$ [VII]

(wherein Ar has the same meaning as above).

Preferred examples of the arylenebisboronic acid are 1,2-phenylenebisboronic acid, 1,3-phenylenebisboronic acid, 1,4-phenylenebisboroic acid, 2-methyl-1,4-phenylenebisboronic acid, 2,5-dimethyl-1,4-phenylenebisboronic acid, 2,3-dimethyl-1,4- phenylenebisboronic acid, 1,4-dimethyl-2,3-phenylenebisboronic acid, 2,3,5,6-tetramethyl-1,4-phenylenebisboronic acid, 2,5-dimethoxy-1,4-phenylenebisboronic acid, 2,5-dihexyloxy-1,4-phenylenebisboronic acid, and 2,5-bis(1-methylheptyloxy)-1,4-phenylenediboronic acid.

The amount of the arylenebisboronic acid to be used for the polycondensation may fall between 0.5 and 2 equivalents, preferably between 0.7 and 1.2 equivalents relative to one equivalent of the 2,7-dihalo-9-oxo-9-phosphafluorene to be reacted with it.

The polycondensation rapidly goes on at a preferred rate in the presence of a palladium catalyst. Various known types of palladium catalyst may be employed, but preferred are low-valence complexes. Especially preferred are 2-valent complexes with a ligand of a tertiary phosphine or tertiary phosphite. Also preferred is an embodiment of using a suitable precursor that may be readily converted into such a low-valence complex in the reaction system.

Still also preferred is an embodiment that comprises mixing a complex not having a tertiary phosphine or phosphite as a ligand with a tertiary phosphine or phosphite to thereby form a low-valence complex having such a ligand of a tertiary phosphine or phosphite in the reaction system. Various types of tertiary phosphines and tertiary phosphites are useful for the ligand of good potency in any of these methods.

Preferred examples of the ligand for use in the reaction are triphenyl phosphine, diphenylmethyl phosphine, phenyldimethyl phosphine, 1,4-bis(diphenylphosphino)butane, 1,3-bis(diphenylphosphino)propane, 1,1'-bis(diphenylphosphino)ferrocene, trimethyl phosphite, and triphenyl phosphite. Complexes with no ligand of a tertiary phosphine or tertiary phosphite, which is used herein as combined or not combined with any of the above-mentioned ligands include, but not limited to, bis(dibenzylideneacetone)palladium, palladium acetate, dichlorobis(benzonitrile)palladium, dichloro(1,5-cyclooctadiene)palladium(II), palladium(II) bishexafluoropentanedionate, and palladium(II) bispentanedionate. Preferred examples of phosphine or phosphite complexes for use herein are dimethylbis(triphenylphosphine)palladium, dimethylbis(diphenylmethylphosphine)palladium, dimethylbis(dimethylphenylphosphine)palladium, dimethylbis(triethylphosphine)palladium, (ethylene)bis(triphenylphosphine)palladium, tetrakis(triphenylphosphine)palladium, bis(tricyclohexylphosphine)palladium, and dichlorobis(triphenylphosphine)palladium.

The amount of the palladium complex to be used herein falls between 0.00001 and 20 equivalents, preferably between 0.0001 and 2 equivalents relative to one equivalent of the starting 2,7-dihalo-9-oxo-9-phosphafluorenone.

Preferably, the coupling reaction with the palladium complex is promoted by a base. For it, various types of inorganic or organic bases may be used. Their examples are lithium carbonate, sodium carbonate, potassium carbonate, lithium hydroxide, sodium hydroxide, potassium hydroxide, lithium oxide, sodium acetate, potassium acetate, magnesium oxide, calcium oxide, barium hydroxide, trilithium phosphate, trisodium phosphate, tripotassium phosphate, cesium fluoride, cesium carbonate, aluminium oxide, trimethylamine, triethylamine, N,N,N',N'-tetramethylethylenediamine, diisopropylamine, diisopropylethylamine, N-methylpiperidine, 2,2,6,6-tetramethyl-N-methylpiperidine, pyridine, 4-dimethylaminopyridine, N-methylmorpholine, sodium ethoxide, and potassium tert-butoxide. The amount of the base to be used falls between 1 and 100 equivalents, preferably between 2 and 20 equivalents, relative to one equivalent of the starting 2,7-dihalo-9-oxo-9-phosphafluorene.

The reaction may be effected at various temperatures, but is generally effected at a temperature falling between −70 and 180° C., preferably between 0 and 150° C.

Preferably, the reaction is effected in a solvent. Examples of the solvent are N,N-dimethylformamide, hexamethylphosphoryl triamide, toluene, benzene, chloroform, tetrahydrofuran and water. For promoting the polycondensation, the amount of the solvent to be used is not specifically defined, but generally falls between 0.1 and 100 mL, preferably between 1 and 20 mL, relative to 1 mmol of the starting 2,7-dihalo-9-oxo-9-phosphafluorene.

After the reaction, the reaction mixture may be post-treated through per-se known extrusion crystallization, filtration or washing with water, and the reaction product may be readily isolated and purified through reprecipitation or the like.

The polymer of formula [V] may be produced through polycondensation, known as Heck reaction, of the 2,7-dihalo-9-oxo-9-phosphafluorene of formula [VI] with an olefin of the following general formula [VIII]:

[VIII]

(wherein R' has the same meaning as above).

The polycondensation efficiently goes on in the presence of a transition metal-based chemical substance, especially that generally used in Heck reaction. The transition metal is preferably a latter-period transition metal of Groups 8 to 10 of the Periodic Table. More effective are low-valence transition metal-based chemical substances, especially those including nickel and palladium. The low-valence transition metal-based chemical substances for use herein may be previously prepared ones. Apart from it, also preferred is another embodiment of using a suitable precursor capable of being readily converted into a low-valence transition metal-based chemical substance in the reaction system. The transition metal-based chemical substances that are used in the invention in any embodiment of using the previously-prepared one or using a precursor of the compound are, for example, simple substances of metal such as metal powder; metals carried by activated charcoal or the like; and metal salts or metal complexes with various types of ligand. Preferred for use herein are complexes with a ligand of tertiary phosphines, tertiary phosphites, imines or pyridine derivatives, as well as other chemical compounds prepared by adding any of these ligands to the above-mentioned metals of latter period of the Periodic Table.

Preferred examples of the ligand for use in the reaction are triphenyl phosphine, diphenylmethyl phosphine, phenyldimethyl phosphine, tri(2-furyl) phosphine, 1,4-bis(diphenylphosphino)butane, 1,3-bis(diphenylphosphino)propane, 1,1'-bis(diphenylphosphino)ferrocene, trimethyl phosphite, triphenyl phosphite, dimethyl phenylphosphonous, dimethyl methylphosphinous, ethylene-1,2-bisoxazoline, diphenylphosphinomethyloxazoline, pyridine, 1,1'-dipyridyl, and orthophenanthroline.

Preferred examples of the transition metal compound, which is used in the invention as a previously-prepared one or in the form of its precursor, include, but are not limited to, palladium powder, activated charcoal-carried palladium, bis (dibenzylideneacetone)palladium, palladium chloride, palladium acetate, dichlorobis(benzonitrile)palladium, dichloro(1,5-cyclooctadiene)palladium(II), palladium(II) bishexafluoropentanedionate, palladium(II) bispentanedionate, dimethylbis(triphenylphosphine)palladium, dimethylbis(diphenylmethylphosphine)palladium, dimethylbis(dimethylphenylphosphine)palladium, dimethylbis(triethylphosphine)palladium, dimethyl[1,1'-bis(diphenylphosphino)ferrocene]palladium, dimethyl[1,4-bis(diphenylphosphino)butane]palladium, (ethylene)bis(triphenylphosphine)palladium, tetrakis(triphenylphosphine)palladium, bis(tricyclohexylphosphine)palladium, dichlorobis(triphenylphosphine)palladium, dichloro(orthophenanthroline)palladium, dichloro[ethylene-1,2-bisoxazoline]palladium, and dichlorobis(triphenylphosphine)nickel.

The amount of the transition metal-based chemical substance to be used herein falls between 0.00001 and 20 equivalents, preferably between 0.0001 and 2 equivalents relative to one equivalent of the starting 2,7-dihalo-9-oxo-9-phosphafluorene.

Preferably, the reaction is promoted by a base. For it, various types of inorganic or organic bases may be used. Their examples are lithium carbonate, sodium carbonate, potassium carbonate, sodium acetate, potassium acetate, magnesium oxide, calcium oxide, trimethylamine, triethylamine, tributylamine, N,N,N',N'-tetramethylethylenediamine, diisopropylamine, diisopropylethylamine, dicyclohexylmethylamine, N-methylpiperidine, 2,2,6,6-tetramethyl-N-methylpiperidine, pyridine, 4-dimethylaminopyridine, and N-methylmorpholine. The amount of the base to be used may be far excessive over the reactants, but generally falls between 1 and 100 equivalents, preferably between 2 and 20 equivalents relative to the starting 2,7-dihalo-9-oxo-9-phosphafluorene.

The amount of the olefin to be used for starting the reaction is not specifically defined, but, in general, it is preferably at least 0.5 equivalents, more preferably from 0.95 to 200 equivalents relative to 2,7-dihalo-9-oxo-9-phosphafluoene for realizing a higher degree of polymerization. When the olefin is gaseous at room temperature, its pressure shall be determined depending on the solubility and the reactivity of the gaseous olefin, but in general, it may fall between 0.1 and 100 atmospheres, preferably between 0.5 and 10 atmospheres.

The reaction may be effected at various temperatures, but is generally effected at a temperature falling between −70 and 180° C., preferably between 0 and 150° C.

Preferably, the reaction is effected in a solvent. Examples of the solvent are N,N-dimethylformamide, hexamethylphosphoryl triamide, xylene, toluene, benzene, tetrahydrofuran, and dibutyl ether. For promoting the polycondensation, the amount of the solvent to be used is not specifically defined, but generally falls between 0.1 and 100 mL, preferably between 0.3 and 10 mL relative to 1 mmol of the starting 2,7-dihalo-9-oxo-9-phosphafluorene. When the base used herein is liquid, its amount may be far excessive over the reactants so that the excess liquid base may serve as a solvent for the reaction. This is also another preferred embodiment of the invention.

After the reaction, the reaction mixture may be post-treated through per-se known extrusion crystallization, filtration or washing with water, and the reaction product may be readily isolated and purified through reprecipitation or the like.

The starting compound, 2,7-dihalo-9-oxo-9-phosphafluoene compound in the production method of the invention is obtained by halogenating a 9-oxo-9-phosphafluorene of the following general formula [IX]

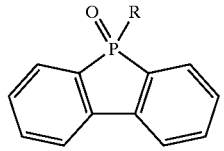

[IX]

(wherein R has the same meaning as above), with a halogen molecule.

For the reaction, preferably used is molecular chlorine, bromine or iodine. The amount of the halogen molecule to be used must be at least 2 equivalents relative to the 9-oxo-9-phosphafluorene of formula [IX], but may be excess over it.

The reaction effectively goes on in the presence of a Lewis acid catalyst. The Lewis acid catalyst may be any one generally used in aromatic electrophilic substitution. Concretely, it includes, for example, aluminium chloride, aluminium bromide, iron chloride, and antimony chloride. Metals that are the precursors for them may also be used, including, for example, metal aluminium and metal iron. The amount of the catalyst to be used may be at least one equivalent relative to the starting 9-oxo-9-phosphafluorene of formula [IX], but may be a catalytic amount thereof for efficient reaction.

The reaction may be effected at various temperatures, but is generally effected at a temperature falling between −70 and 180° C., preferably between 0 and 150° C.

No solvent may be used in the reaction. However, when the starting 9-oxo-9-phosphafluorene is solid, it may be dissolved in a solvent. For the solvent, for example, preferred are halogenohydrocarbons; carboxylic acids such as acetic acid; carbon disulfide; and aromatic nitro compounds such as nitrobenzene.

The product may be readily isolated and purified in any ordinary manner, for example, through recrystallization or chromatography.

2,7-Dihalo-9-oxo-9-phosphafluorene compounds of formula [VI] are novel compounds, not disclosed in any literature.

The polymer of the invention can be formed into thin films in any simple working technique of, for example, spin coating or casting, and it is useful as a component of organic thin-film electrochromic elements and organic luminescent elements.

The invention is described more concretely with reference to the following Examples, which, however, are not intended to restrict the scope of the invention.

EXAMPLES

Example 1

In a nitrogen atmosphere, 0.336 g (1.2 mmols) of bis(1,5-cyclooctadiene)nickel, 0.2 mL of 1,5-cyclooctadiene, 0.200 g (1.3 mmols) of α,α'-dipyridyl, and 0.484 g (1.0 mmol) of 2,7-dibromo-9-nonyl-9-oxo-9-phosphafluorene (of formula [VI] where R is n-nonyl group and X is bromine) were added to 20 mL of N,N-dimethylformamide, and stirred under heat at 60° C. for 48 hours. The reaction mixture was poured into 100 mL of 0.5 M diluted hydrochloric acid, and the resulting powder was taken out through filtration. The powder was washed with 50 mL of water, then dissolved in 5 mL of chloroform, and reprecipitated in 100 mL of methanol to thereby isolate 0.295 g (0.91 mmols in terms of the monomer unit) of a polymer having repeating units of a 9-nonyl-9-oxo-9-phosphafluorene-2,7-diyl group (of formula [III] where R is nonyl group). Thus obtained, the polymer is a novel compound not disclosed in any literature. Calculated through gel permeation chromatography (GPC method), its number-average molecular weight was 3980 and its weight-average molecular weight was 8025.

Its NMR spectral data and elementary analysis data are mentioned below.

$^1$H-NMR(CDCl$_3$): δ0.83(3H,brs),1.22(10H,brs),1.37(2H,brs),1.61(2H,brs),2.17(2H,brs), 7.87(4H,brs),8.09(2H, brs). $^{31}$P-NMR(CDCl$_3$): δ43.7. Elementary Analysis: Calculated as n=12 (C$_{252}$H$_{301}$O$_{12}$P$_{12}$Br): C, 76.17; H, 7.63; Br, 2.01. Found: C, 75.93; H, 7.88; Br, 2.22.

Example 2

In the same manner as in Example 1, obtained was 0.251 g (0.81 mmols in terms of the monomer unit) of a polymer having repeating units of a 9-(2-octyl)-9-oxo-9-phosphafluorene-2,7-diyl group (of formula [III] where R is 2-octyl group), for which, however, used was 0.470 g (1.0 mmol) of 2,7-dibromo-9-(2-octyl)-9-oxo-9-phosphafluoene (of formula [VI] where R is 2-octyl group and X is bromine) in place of 2,7-dibromo-9-nonyl-9-oxo-9-phosphafluoene in Example 1. Thus obtained, the polymer is a novel compound not disclosed in any literature. Calculated through gel permeation chromatography method (GPC) method, its number-average molecular weight was 3356 and its weight-average molecular weight was 4679.

Its NMR spectral data and elementary analysis data are mentioned below.

$^1$H-NMR(CDCl$_3$): δ0.84(3H,brs),1.24(9H,brs),1.50(1H,brs),1.72(2H,brs),1.92(1H,brs), 2.34(1H,brs),7.85(4H,brs), 8.05(2H,brs). $^{31}$P-NMR(CDCl$_3$): δ50.2. Elementary Analysis: Calculated as n=10 (C$_{200}$H$_{231}$O$_{10}$P$_{10}$Br): C, 75.43; H, 7.31; Br, 2.51. Found: C, 75.23; H, 7.45; Br, 2.54.

Example 3

In the same manner as in Example 1, obtained was 0.99 g (0.38 mmols in terms of the monomer unit) of a polymer having repeating units of a 9-propyl-9-oxo-9-phosphafluorene-2,7-diyl group (of formula [III] where R is n-propyl group), for which, however, used was 0.200 g (0.50 mmol) of 2,7-dibromo-9-propyl-9-oxo-9-phosphafluoene (of formula [VI] where R is n-propyl group and X is bromine) in place of 2,7-dibromo-9-nonyl-9-oxo-9-phosphafluoene in Example 1, and used were 0.168 g (0.50 mmol) of bis(1,5-cyclooctadiene)nickel, 0.1 mL of 1.5-cyclooctadiene, 0.100 g (0.64 mmol) of α,α'-dipyridyl and 10 mL of N,N-dimethylformamide. Thus obtained, the polymer is a novel compound not disclosed in any literature. Its IR spectrometry confirmed that the polymer is a hydrate. The number-average molecular weight of the polymer calculated through elementary analysis was 3180.

The NMR spectral data and elementary analysis data of the polymer are mentioned below.

$^1$H-NMR(CDCl$_3$): δ1.03(3H,brs),1.64(2H,brs),1.95(2H,brs),2.18(2H,brs),7.74(4H,brs), 8.04(2H,brs). $^{31}$P-NMR (CDCl$_3$): δ43.5. Elementary Analysis: Calculated as n=12 (C$_{180}$H$_{181}$O$_{24}$P$_{12}$Br): C, 67.99; H, 5.74. Found: C, 68.05; H, 5.72.

Example 4

In a nitrogen atmosphere, a mixture of 0.012 g (0.010 mmol) of tetrakis(triphenylphosphine)palladium (0), 0.484 g (1.0 mmol) of 2,7-dibromo-9-nonyl-9-oxo-9-phosphafluorene (of formula [VI] where R is n-nonyl group and X is bromine), 0.367 g (1.0 mmol) of 2,5-dihexyloxy-1,4-phenylenediboronic acid, 2.0 g of tripotassium phosphate and 10 mL of N,N-dimethylformamide was heated at 125° C., and stirred for 48 hours at the temperature. The reaction mixture was poured into 100 mL of water, and the resulting powder was taken out through filtration. The powder was washed with 50 mL of water, then dissolved in 5 mL of chloroform, and reprecipitated in 100 mL of methanol to thereby isolate 0.495 g (0.83 mmols in terms of the monomer unit) of a polymer having in the backbone a 9-nonyl-9-oxo-9-phosphafluorene-2,7-diyl group and a 2,5-dihexyloxy-1,4-phenylene group (of formula [IV] where R is nonyl group and Ar is 2,5-dihexyloxy-1,4-phenylene group). Thus obtained, the polymer is a novel compound not disclosed in any literature. Calculated through gel permeation chromatography method (GPC method), its number-average molecular weight was 10100 and its weight-average molecular weight was 22000. Calculated through elementary analysis, its mean molecular weight was 8290. Its NMR spectral data and elementary analysis data are mentioned below.

$^1$H-NMR(CDCl$_3$): δ0.86(6H,brs),1.31(16H,brs),1.64 (12H,brs),1.77(2H,brs),4.02(4H,brs), 7.10(2H,m),7.84–7.87 (2H,m),7.83–7.93(2H,m),8.09(2H,d,J=9.3 Hz). $^{31}$P-NMR (CDCl$_3$): δ43.9. Elementary Analysis: Calculated as n=13 (C$_{528}$H$_{714}$O$_{40}$P$_{14}$Br$_2$): C, 76.45; H, 8.68; Br, 1.93. Found: C, 76.61; H, 8.83; Br, 2.20.

Example 5

In the same manner as in Example 4, obtained was 0.460 g (0.89 mmols in terms of the monomer unit) of a polymer having in the backbone a 9-oxo-9-phosphor-9-propylfluorene-2,7-diyl group and a 2,5-dihexyloxy-1,4-phenylene group (of formula [IV] where R is propyl group and Ar is 2,5-dihexyloxy-1,4-phenylene group), for which, however, used was 0.400 g (1.0 mmol) of 2,7-dibromo-9-oxo-9-phosphor-9-propylfluorene (of formula [VI] where R is n-propyl group and X is bromine) in place of 2,7-dibromo-9-nonyl-9-oxo-9-phosphafluorene. Thus obtained, the polymer is a novel compound not disclosed in any literature. Calculated through GPC method, the number-average molecular weight of the THF-soluble part of the polymer was 6230 and the weight-average molecular weight thereof was 8980. Calculated through elementary analysis, the mean molecular weight of the polymer was 9090.

The NMR spectral data and elementary analysis data of the polymer are mentioned below.

$^1$H-NMR(CDCl$_3$): δ0.87(6H,brs),0.99(3H,brs),1.31(2H,brs),1.77(6H,brs),2.13(2H,brs,),3.98(4H,brs), 6.98(2H,s), 7.87(4H,m),8.09(2H,d,J=8.0 Hz). $^{31}$P-NMR(CDCl$_3$): δ44.0. Elementary Analysis: Calculated as n=14 (C$_{477}$H$_{587}$O$_{43}$P$_{15}$Br$_2$): C, 74.94; H, 7.73; Br, 2.10. Found: C, 74.73; H, 7.88; Br, 1.76.

Example 6

In the same manner as in Example 4, obtained was 0.319 g (0.80 mmol in terms of the monomer unit) of a polymer having in the backbone a 9-nonyl-9-oxo-9-phosphafluorene-2,7-diyl group and a 1,4-phenylene group (of formula [IV] where R is nonyl group and Ar is 1,4-phenylene group), for which, however, used was 0.166 g (1.0 mmol) of 1,4-phenylenediboronic acid in place of 2,5-dihexyloxy-1,4-phenylenediboronic acid. Thus obtained, the polymer is a novel compound not disclosed in any literature. Calculated through GPC method, the number-average molecular weight of the THF-soluble part of the polymer was 2110 and the weight-average molecular weight thereof was 2380. Calculated through elementary analysis, the mean molecular weight of the polymer was 4090. The NMR spectral data and elementary analysis data of the polymer are mentioned below.

$^1$H-NMR(CDCl$_3$): δ0.83(3H,brs),1.20(10H,brs),1.61(2H, brs),2.15(2H,brs),7.47(2H,m), 7.65–7.87(6H,m),8.14(2H, m). $^{31}$P-NMR(CDCl$_3$): δ43.9. Elementary Analysis: Calculated as n=9 (C$_{264}$H$_{286}$O$_{10}$P$_{10}$Br$_2$): C, 77.55; H, 7.05; Br, 3.91. Found: C, 77.37; H, 7.10; Br, 3.98.

Example 7

0.0012 g (0.010 mmol) of palladium acetate, 0.0061 g (0.020 mmol) of tri-o-tolylphosphine, 0.43 mL of tri-n-butylamine, 0.235 g (0.50 mmol) of 2,7-dibromo-9-(2-octyl)-9-oxo-9-phosphafluorene (of formula [VI] where R is 2-octyl group and X is bromine) and 0.5 mL of N,N-dimethylformamide were put into a glass reactor. The reaction system was connected to a normal-pressure ethylene reactor, via which it was charged with ethylene. Then, the glass reactor was dipped in an oil bath at 125° C. and its contents were stirred under heat for 48 hours. The reaction mixture was poured into 100 mL of 0.5 M diluted hydrochloric acid, and the resulting powder was taken out through filtration. The powder was washed with 50 mL of water, then dissolved in 5 mL of chloroform, and reprecipitated in 100 mL of diethyl ether to thereby isolate 0.077 g (0.23 mmol in terms of the monomer unit) of a polymer having repeating units of a 9-(2-octyl)-9-oxo-9-phosphafluoene-2,7-diyl group and a vinylene group (of formula [V] where R is 2-octyl group). Thus obtained, the polymer is a novel compound not disclosed in any literature. Calculated through gel permeation chromatography, the number-average molecular weight of the polymer was 1530 and the weight-average molecular weight thereof was 2540.

The NMR spectral data and elementary analysis data of the polymer are mentioned below.

$^1$H-NMR(CDCl$_3$): δ0.84(6H,brs),1.03(2H,brs),1.23(6H, brs),1.47(1H,brs),1.86(1H,brs), 2.28(1H,brs),6.94–8.46(8H, m). $^{31}$P-NMR(CDCl$_3$): δ50.4. Elementary Analysis: Calculated as n=5 (C$_{130}$H$_{148}$O$_6$P$_6$Br$_2$): C, 72.55; H, 6.93. Found: C, 72.15; H, 7.27.

Example 8

In the same manner as in Example 7, obtained was 0.112 g (0.39 mmol in terms of the monomer unit) of a polymer having repeating units of a 9-propyl-9-oxo-9-phosphafluorene-2,7-diyl group and a vinylene group (of formula [V] where R is n-propyl group), for which, however, used was 0.200 g (0.50 mmol) of 2,7-dibromo-9-propyl-9-oxo-9-phosphafluorene (of formula [VI] where R is n-propyl group and X is bromine) in place of 2,7-dibromo-9-(2-octyl)-9-oxo-9-phosphafluorene in Example 7. Thus obtained, the polymer is a novel compound not disclosed in any literature. Its IR absorptiometry confirmed that the polymer is a hydrate. Calculated through elementary analysis, the number-average molecular weight of the polymer was 2410.

The NMR spectral data and elementary analysis data of the polymer are mentioned below.

$^1$H-NMR(CDCl$_3$): δ0.99(3H,brs),1.35(2H,brs),1.76(2H, brs),2.14(2H,m),7.23(2H,s), 7.43–8.04(6H,m). $^{31}$P-NMR (CDCl$_3$): δ43.6. Elementary Analysis: Calculated as n=7 (C$_{134}$H$_{134}$O$_{16}$P$_8$Br$_2$): C, 66.84; H, 5.61. Found: C, 66.96; H, 6.05.

Example 9

In the same manner as in Example 7, obtained was 0.114 g (0.40 mmol in terms of the monomer unit) of a polymer having repeating units of a 9-propyl-9-oxo-9-phosphafluorene-2,7-diyl group and a vinylene group (of formula [V] where R is n-propyl group), for which, however, used was xylene in place of N,N-dimethylformamide in Example 8. Thus obtained, the polymer is a novel compound not disclosed in any literature. Its IR absorptiometry confirmed that the polymer is a hydrate. Calculated through elementary analysis, the number-average molecular weight of the polymer was 3260.

The NMR spectral data and elementary analysis data of the polymer are mentioned below.

$^1$H-NMR(CDCl$_3$): δ0.98(3H,brs),1.37(2H,brs),1.97(2H, brs),2.14(2H,m),7.20(2H,s), 7.57–8.16(6H,m). $^{31}$P-NMR (CDCl$_3$): δ43.4. Elementary Analysis: Calculated as n=10 (C$_{185}$H$_{185}$O$_{22}$P$_{11}$Br$_2$): C, 68.14; H, 5.72. Found: C, 68.04; H, 6.12.

Example 10

12.3 mL of bromine was added to a mixture 5.88 g (24.3 mmol) of 9-oxo-9-phospha-9-propylfluorene (of formula [IX] where R is n-propyl group) and 0.243 g (4.35 mmol) of iron powder within a period of 30 minutes, and stirred under heat at 65° C. for 24 hours. The reaction mixture was mixed with 500 mL of water, and extracted with 500 mL of chloroform. The resulting chloroform extract was washed with 200 mL of saturated sodium thiosulfate. Then, this was dried with magnesium sulfate anhydride, and concentrated, and the resulting solid was recrystallized from methanol to thereby isolate 6.32 g (15.8 mmol) of 2,7-dibromo-9-oxo-9-phospha-9-propylfluorene (of formula [VI] where R is n-propyl group). Thus obtained, the compound was a colorless tabular crystal, and is a novel compound not disclosed in any literature. Its IR and NMR spectral data, melting point and elementary analysis data are mentioned below.

IR(KBr): 2956.3,2933.2,2875.3,1456.0,1394.3,1174.4, 1072.2,817.7 cm$^{-1}$. $^1$H-NMR(CDCl$_3$): δ1.00(3H,t,J=7.3 Hz),1.50–1.59(2H,m),2.04–2.14(2H,m), 7.61(2H,dd,J=1.9, 8.3 Hz),7.71(2H,dd,J=0.6,8.3 Hz),7.92(2H,dd,J=1.6,9.2 Hz). $^{13}$C-NMR(CDCl$_3$): δ15.5(d,J=16.8 Hz),15.9(d,J=3.5 Hz),32.3(d,J=69.7 Hz), 122.8(d,J=10.1 Hz),123.6(d,J=13.7 Hz),132.4(d,J=10.3 Hz),134.0(d,J=98.4 Hz), 136.3(d,J=1.9 Hz),139.0(d,J=9.98 Hz). $^{31}$P-NMR(CDCl$_3$): δ42.2. m.p.: 226.0–226.4° C. Elementary Analysis: Calculated as C$_{15}$H$_{13}$OPBr$_2$: C, 45.04; H, 3.28. Found: C, 45.08; H, 3.10.

Example 11

In the same manner as in Example 9, obtained was 5.63 g (11.6 mmol) of 2,7-dibromo-9-nonyl-9-oxo-9-phosphafluoene (of formula [VI] where R is nonyl groups), for which, however, used was 7.93 g (24.3 mmol) of 9-nonyl-9-oxo-9-phosphafluorene (of formula [IX] where R is nonyl groups) in place of 9-oxo-9-phospha-9-propylfluorene in Example 10. Thus obtained, the compound was a colorless acicular crystal, and is a novel compound not disclosed in any literature.

Its IR and NMR spectral data, melting point and elementary analysis data are mentioned below.

IR(KBr): 2952.5,2921.6,2850.7,1454.1,1394.3,1176.4, 1089.6,821.5 cm$^{-1}$. $^1$H-NMR(CDCl$_3$): δ0.86(3H,t,J=6.7 Hz),1.21–1.27(10H,m),1.28–1.33(2H,m), 1.47–1.53(2H,m), 2.03–2.13(2H,m),7.61(2H,dd,J=2.3,8.0 Hz),7.70(2H,dd,J= 0.6,8.0 Hz), 7.92(2H,dd,J=1.5,9.2 Hz). $^{13}$C-NMR(CDCl$_3$): δ14.1,21.9(d,J=18.9 Hz),22.6,28.9,29.2,29.3,30.0(d,J=69.8 Hz), 30.8(d,J=15.5 Hz),31.8,122.8(d,J=10.1 Hz),123.7(d,J= 13.6 Hz),132.4(d,J=10.3 Hz), 134.0(d,J=98.6 Hz),136.5(d, J=1.8 Hz),139.0(d,J=19.5 Hz). $^{31}$P-NMR(CDCl$_3$): δ42.5. m.p.: 95.0–96.0° C. Elementary Analysis: Calculated as C$_{21}$H$_{25}$OPBr$_2$: C, 52.09; H, 5.20. Found: C, 52.21; H, 5.11.

Example 12

In the same manner as in Example 10, obtained was 5.35 g (11.4 mmol) of 2,7-dibromo-9-(2-octyl)-9-oxo-9- phosphafluoene (of formula [VI] where R is 2-octyl group), for which, however, used was 7.59 g (24.3 mmol) of 9-(2-octyl)-9-oxo-9-phosphafluorene (of formula [IX] where R is 2-octyl group) in place of 9-oxo-9-phospha-9-propylfluorene in Example 10. Thus obtained, the compound was a colorless acicular crystal, and is a novel compound not disclosed in any literature.

Its IR and NMR spectral data, melting point and elementary analysis data are mentioned below.

IR(KBr): 2950.6,2925.5,2854.1,1450.2,1392.4,1172.5, 1085.7,821.5 cm$^{-1}$. $^1$H-NMR(CDCl$_3$): δ0.84(3H,t,J=6.0 Hz),1.00(3H,dd,J=6.9,18.9 Hz), 1.21(8H,brs), 1.43–1.46 (1H,m),1.74–1.80(1H,m),2.19–2.24(1H,m),7.57(2H,dd,J= 2.8,8.2 Hz), 7.67(2H,d,J=8.2 Hz),7.86(2H,dd,J=2.1,8.9 Hz). $^{13}$C-NMR(CDCl$_3$): δ12.2,14.0,22.5,27.3,27.5,28.8, 31.6,33.6(d,J=69.7 Hz), 122.8(d,J=9.8 Hz),123.5(dd,J=4.0, 13.3 Hz),132.8(dd,J=9.9,16.9 Hz), 132.9(dd,J=29.7,94.8 Hz),136.3,139.8(dd,J=11.6,18.3 Hz). $^{31}$P-NMR(CDCl$_3$): δ49.2. m.p.: 84.4–85.2° C. Elementary Analysis: Calculated as C$_{20}$H$_{23}$OPBr$_2$: C, 51.09; H, 4.93. Found: C, 50.89; H, 5.14.

Example 13

In the same manner as in Example 1, obtained was 0.229 g (0.74 mmol in terms of the monomer unit) of a polymer having repeating units of a 9-(3-ethylhexyl)-9-oxo-9-phosphafluorene-2,7-diyl group (of formula [III] where R is 3-ethylhexyl group), for which, however, used was 0.470 g (1.0 mmol) of 2,7-dibromo-9-(3-ethylhexyl)-9-oxo-9-phosphafluoene (of formula [VI] where R is 3-ethylhexyl group and X is bromine) in place of 2,7-dibromo-9-nonyl-9-oxo-9-phosphafluoene in Example 1. Thus obtained, the polymer is a novel compound not disclosed in any literature. Calculated through gel permeation chromatography method (GPC method), its number-average molecular weight was 5680 and its weight-average molecular weight was 6250.

Its NMR spectral data are mentioned below.

$^1$H-NMR(CDCl$_3$): δ0.76(6H,brs),1.21(4H,brs),1.33(4H, brs),1.67(1H,brs),2.16(2H,brs), 7.85(4H,brs),8.10(2H,brs). $^{31}$P-NMR(CDCl$_3$): δ44.1.

Example 14

Reaction with Catalytic Amount of Ni Salt/Zinc

In a nitrogen atmosphere, 0.0016 g (0.0125 mmol) of nickel chloride, 0.0020 g (0.00125 mmol) of α,α'-dipyridyl, 0.0031 g (0.50 mmol) of zinc powder, and 0.00627 g (0.125 mmol) of 2,7-dibromo-9-nonyl-9-oxo-9-phosphafluorene (of formula [VI] where R is nonyl group and X is bromine) were dissolved in N,N-dimethylformamide, to which was added 1.6 μL (0.0125 mmol) of chlorotrimethylsilane, and stirred under heat at 100° C. for 48 hours. The reaction mixture was poured into 20 mL of 0.5 diluted hydrochloric acid, and the resulting powder was taken out through filtration. The powder was washed with 10 mL of water, then dissolved in 1 mL of chloroform, and reprecipitated in 10 mL of methanol to thereby obtain 33 mg (0.108 mmol in terms of the monomer unit) of a polymer having repeating units of a 9-nonyl-9-oxo-9-phosphafluorene-2,7-diyl skeleton (of formula [III] where R is nonyl group). Calculated through GPC method, the number-average molecular weight of the polymer was 2730 and the weight-average molecular weight thereof was 3720.

Example 15

In the same manner as in Example 4, obtained was 0.264 g (0.47 mmol in terms of the monomer unit) of a polymer having in the backbone a 9-(2-octyl)-9-oxo-9-phosphafluorene-2,7-diyl group and a 2,5-dihexyloxy-1,4-phenylene group (of formula [IV] where R is 2-octyl group and Ar is 2,5-dihexyloxy-1,4-phenylene group), for which, however, used was 0.235 g (0.50 mmol) of 2,7-dibromo-9-(2-octyl)-9-oxo-9-phosphafluorene (of formula [VI] where R is 2-octyl group and X is bromine) in place of 2,7-dibromo-9-nonyl-9-oxo-9-phosphafluorene in Example 4, and used were 0.0058 g (0.0050 mmol) of tetrakis (triphenylphosphine)palladium, 0.184 g (0.50 mmol) of 2,5-dihexyloxy-1,4-phenylenediboronic acid, 1.0 g of tripotassium phosphate and 5 mL of N,N-dimethylformamide. Thus obtained, the polymer is a novel compound not disclosed in any literature. Calculated through GPC method, the number-average molecular weight of the polymer was 19400 and the weight-average molecular weight thereof was 22000. Calculated through elementary analysis, the mean molecular weight of the polymer was 13400.

The NMR spectral data and elementary analysis data of the polymer are mentioned below.

$^1$H-NMR(CDCl$_3$): δ0.87(9H,brs),1.08(3H,dd,J=6.1,18.2 Hz),1.36(18H,brs),1.73(7H,m), 2.00(1H,brs),2.33(2H,brs), 2.95(4H,brs),7.09(2H,s),7.85(2H,m),7.96(2H,m),8.04(2H, m). $^{31}$P-NMR(CDCl$_3$): δ51.3. Elementary Analysis: Calculated as n=22 (C$_{856}$H$_{1145}$O$_{67}$P$_{23}$Br$_2$): C, 76.84; H, 8.63; Br, 1.20. Found: C, 76.38; H, 8.65; Br, 1.20.

Example 16

In the same manner as in Example 10, obtained was 11.7 g (24.8 mmol) of 2,7-dibromo-9-(3-ethylhexyl)-9-oxo-9-phosphafluoene (of formula [VI] where R is 3-ethylhexyl group), for which, however, used was 12.5 g (40.0 mmol) of 9-(3-ethylhexyl)-9-oxo-9-phosphafluorene (of formula [IX] where R is 3-ethylhexyl) in place of 9-oxo-9-phospha-9-propylfluorene in Example 10. Thus obtained, the compound was a colorless acicular crystal, and is a novel compound not disclosed in any literature.

Its IR and NMR spectral data, melting point and elementary analysis data are mentioned below.

IR(KBr): 2958.3,2923.6,2856.1,1442.4,1390.4,1184.1, 1085.7,817.7 cm$^{-1}$. $^1$H-NMR(CDCl$_3$): δ0.79(3H,t,J=7.4 Hz)0.83(3H,t,J=7.0 Hz),1.12–1.17(4H,m), 1.28–1.32(2H, m),1.37–1.43(2H,m),1.65–1.71(1H,m)2.01–2.13(2H,m), 7.60(2H,dd,J=2.9,8.2 Hz),7.69(2H,d,J=8.3 Hz),7.92(2H,dd, J=1.6,9.1 Hz). $^{13}$C-NMR(CDCl$_3$): δ10.3,14.0,22.7,27.4(d, J=8.8 Hz),28.8,34.0(d,J=8.2 Hz), 34.3(d,J=69.2 Hz),34.4(d, J=3.1 Hz),122.7(d,J=10.3 Hz),123.6(dd,J=4.1,13.5 Hz), 132.5(d,J=10.4 Hz),134.5(dd,J=15.5,97.3 Hz),136.2,138.9 (dd,J=3.1,19.7 Hz). $^{31}$P-NMR(CDCl$_3$): δ42.7. m.p.: 139.1–139.8° C. Elementary Analysis: Calculated as C$_{20}$H$_{23}$OPBr$_2$: C, 51.09; H, 4.93. Found: C, 50.86; H, 5.14.

Example 17

The solubility (1 mg polymer/1 mL solvent) of the polymers obtained in Examples 1 to 9, 13 and 15 in different solvents was evaluated.

The results are shown in Tables 1 to 4. Regarding the criteria for evaluation, soluble samples are indicated by (⊙); partly soluble samples are by {○ or Δ, but ○>Δ in point of the solubility); and insoluble samples are by (x).

TABLE 1

Solubility of Polymers

| Polymer | CHCl$_3$ | THF | methanol | toluene |
|---|---|---|---|---|
| Example 1 | ⊙ | ○ | Δ | x |
| Example 2 | ⊙ | ○ | Δ | x |
| Example 3 | Δ | Δ | x | x |

TABLE 2

Solubility of Polymers

| Polymer | CHCl$_3$ | THF | ethanol | toluene |
|---|---|---|---|---|
| Example 4 | ⊙ | ⊙ | ○ | Δ |
| Example 5 | ⊙ | ○ | Δ | x |
| Example 6 | ⊙ | Δ | x | x |

TABLE 3

Solubility of Polymers

| Polymer | CHCl$_3$ | THF | methanol | toluene |
|---|---|---|---|---|
| Example 7 | ⊙ | Δ | Δ | x |
| Example 8 | ○ | Δ | Δ | x |
| Example 9 | ○ | Δ | x | x |

TABLE 4

Solubility of Polymers

| Polymer | CHCl$_3$ | THF | methanol | toluene |
|---|---|---|---|---|
| Example 13 | ⊙ | Δ | x | x |
| Example 15 | ⊙ | ○ | Δ | x |

Example 18

The optical properties of the polymers obtained in Examples 1 to 9, 13 and 15 were evaluated. The matters tested for these are the absorption peak wavelength in the UV range (UVλmax), the molar extinction coefficient per the monomer unit (ε), the fluorescent spectrum peak wavelength in UV exposure (EMλmax), and the quantum efficiency in solution.

The results are given in Table 5.

TABLE 5

Optical Properties of Polymers

| | Optical Properties | | | | | |
|---|---|---|---|---|---|---|
| | Solution in CHCl$_3$ | | | | Thin Film | |
| Polymer | UVλmax (nm) | EMλmax (nm) | ε (M$^{-1}$cm$^{-1}$) | quantum efficiency | UVλmax (nm) | EMλmax (nm) |
| Example 1 | 387 | 443 | 24700 | 0.59 | 398 | 447 |
| Example 2 | 390 | 444 | 23900 | 0.63 | 398 | 475 |
| Example 3 | 383 | 442 | 17553 | 0.73 | * | * |
| Example 4 | 384 | 431 | 25700 | 0.76 | 390 | 472 |
| Example 5 | 386 | 433 | 29400 | 0.72 | 395 | 465 |
| Example 6 | 378 | 413 | 31800 | 0.81 | 386 | 457 |
| Example 7 | 400 | 456 | 16300 | 0.74 | 433 | 539 |
| Example 8 | 408 | 455 | 19100 | 0.78 | 420 | 536 |
| Example 9 | 400 | 456 | 17600 | 0.77 | 408 | 538 |
| Example 13 | 390 | 443 | 28500 | 0.81 | 399 | 481 |
| Example 15 | 386 | 432 | 29200 | 0.68 | 387 | 465 |

*: not detected.

As is known from Table 5, the polymers obtained in Examples 1 to 9, 13 and 15 all emit fluorescence having a peak wavelength in the visible light range in any form of solution in CHCl₃ and thin film, and their quantum efficiency in solution in CHCl₃ is high, falling between 0.59 and 0.81.

Example 19

Electrochromic Element Formed of Polymer

This is to demonstrate the spectral electrochemical response of the polymer obtained in Example 4. One mg of the polymer was dissolved in 200 µL of dichloroethane, and the resulting polymer solution was cast on a commercially-available transparent electrode (50×5 mm) to prepare a working electrode. This was disposed in a quartz cell along with a counter electrode (platinum plate) and a reference electrode (silver, silver ion electrode). With that, the cell was filled with a supporting electrolyte, tetrabutylammonium perchlorate, and a solvent, dewatered acetonitrile. The cell was driven, and the color change of the polymer owing to the potential change in the cell was detected with a spectrophotometer. As a result, it was found that the thin film of the polymer of Example 4 was pale yellow in neutral but changed from pale yellow to deep violet with the increase in the potential applied to the cast film of the polymer. With the change, the UV absorption band intrinsic to the polymer that had existed at around 390 nm disappeared, and a novel visible light absorption band appeared at around 570 nm.

INDUSTRIAL APPLICABILITY

The present invention provides a polymer which contains in the backbone a 9-oxo-9-phosphafluorene-2,7-diyl skeleton or a combination of the skeleton and an arylene or vinylene group and which is useful, for example, as a component of a luminescent element or electrochromic element, and provides a process for producing the polymer.

The invention also provides a 2,7-dihalo-9-oxo-9-phosphafluorene compound which is useful, for example, as a monomer for producing functional polymers, and provides a process for producing the compound.

What is claimed is:

1. A polymer that contains in the backbone a 9-oxo-9-phosphafluorene-2,7-diyl skeleton or a combination of the skeleton and a vinylene or arylene skeleton of the following general formula [I]:

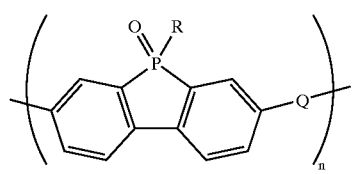

[I]

wherein —Q— represents a single bond, —Ar— (Ar is an arylene group), or a vinylene group of the following general formula [II]:

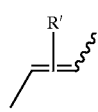

[II]

in which R' represents a hydrogen atom, an optionally-substituted alkyl, cycloalkyl, aryl or aralkyl group, a cyano group, or an alkoxycarbonyl group, and it may bond to any carbon of the olefin chain in the formula;

R represents a hydrogen atom, or an optionally-substituted alkyl, cycloalkyl, aralkyl, aryl, alkoxy, cycloalkyloxy, aralkyloxy or aryloxy group; and n indicates an integer of from 3 to 30000.

2. The polymer as claimed in claim 1, for which -Q- in formula [I] is a single bond and which is represented by the following general formula [III]:

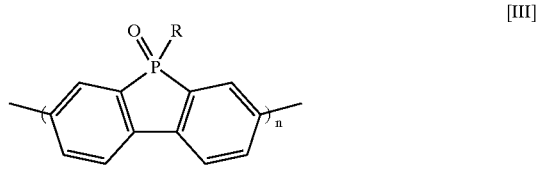

[III]

(wherein R and n have the same meanings as above).

3. The polymer as claimed in claim 1, for which -Q- in formula [I] is —Ar— and which is represented by the following general formula [IV]:

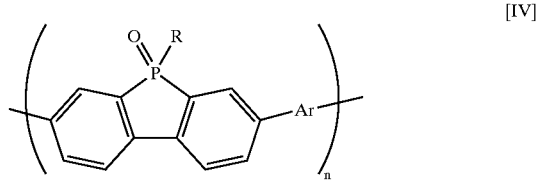

[IV]

(wherein Ar, R and n have the same meanings as above).

4. The polymer as claimed in claim 1, for which -Q- in formula [I] is the vinylene group of formula [II] and which is represented by the following general formula [V]:

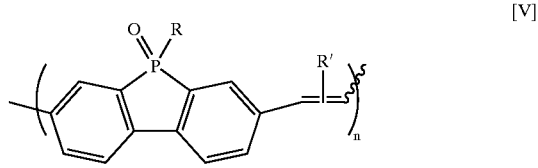

[V]

(wherein R', R and n have the same meanings as above).

5. A process for producing the polymer of claim 1, which comprises dehalo-polycondensing a 2,7-dihalo-9-oxo-9-phosphafluoene of the following general formula [VI]:

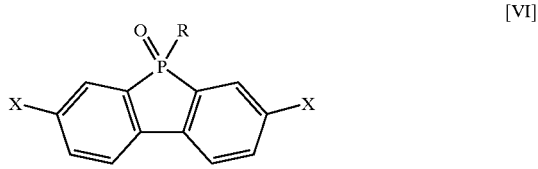

[VI]

(wherein R and X have the same meanings as above), or reacting it with an arylenebisboronic acid followed by polycondensing the resulting intermediate, or polycondensing it with an olefin.

6. The production process as claimed in claim 5, wherein the polycondensation is effected in the presence of a transition metal-based chemical substance.

7. The production process as claimed in claim 6, wherein the transition metal-based chemical substance is a low-valence transition metal-based chemical substance.

8. The production process as claimed in claim 7, wherein the polycondensation is effected in the presence of the low-valence transition metal-based chemical substance formed by adding a reducing agent to a transition metal-based chemical substance of which the valence is not low.

9. The production process as claimed in any of claims 6 to 8, wherein the transition metal is nickel.

10. The production process as claimed in any of claims 6 to 8, wherein the transition metal is palladium.

11. A process for producing the polymer of claim 2, which comprises dehalo-polycondensation of the 2,7-dihalo-9-oxo-9-phosphafluorene of formula [VI].

12. The production process as claimed in claim 11, wherein the polycondensation is effected in the presence of a transition metal-based chemical substance.

13. The production process as claimed in claim 12, wherein the transition metal-based chemical substance is a low-valence transition metal-based chemical substance.

14. The production process as claimed in claim 13, wherein the polycondensation is effected in the presence of the low-valence transition metal-based chemical substance formed by adding a reducing agent to a transition metal-based chemical substance of which the valence is not low.

15. The production process as claimed in any of claims 12 to 14, wherein the transition metal is nickel.

16. A process for producing the polymer of claim 3, which comprises polycondensation of the 2,7-dihalo-9-oxo-9-phosphafluorene of formula [VI] with an arylenebisboronic acid of the following general formula [VII]:

(HO)$_2$B—Ar—B(OH)$_2$ [VII]

wherein Ar has the same meaning as above.

17. The production process as claimed in claim 16, wherein the polycondensation is effected in the presence of a palladium catalyst.

18. The production process as claimed in claim 17, wherein the palladium catalyst is a low-valance complex catalyst.

19. The production process as claimed in claim 17, wherein the palladium catalyst is a divalent complex with a ligand of a tertiary phosphine or tertiary phosphite.

20. The production process as claimed in claim 17, wherein the palladium catalyst is a precursor complex capable of being readily converted into a low-valence complex in the reaction system.

21. The production process as claimed in claim 17, wherein the palladium catalyst is a low-valence complex with a ligand of tertiary phosphine and/or tertiary phosphite that is formed from a combination of a palladium complex not having a ligand of a tertiary phosphine or tertiary phosphite, and a tertiary phosphine and/or a tertiary phosphite in the reaction system.

22. A process for producing the polymer of claim 4, which comprises polycondensation of the 2,7-dihalo-9-oxo-9-phosphafluorene of formula [VI] with an olefin of the following general formula [VIII]:

[VIII]

(wherein R' has the same meaning as above).

23. The production process as claimed in claim 22, wherein the olefin is ethylene.

24. The production process as claimed in claim 22 or 23, wherein the polycondensation is effected in the presence of a transition metal-based chemical substance.

25. The production process as claimed in claim 24, wherein the transition metal-based chemical substance is a low-valence transition metal-based chemical substance.

26. The production process as claimed in claim 25, wherein the polycondensation is effected in the presence of the low-valence transition metal-based chemical substance formed by adding a reducing agent to a transition metal-based chemical substance of which the valence is not low.

27. The production process as claimed in claim 24, wherein the transition metal is palladium.

28. The production process as claimed in claim 27, wherein the palladium catalyst is a divalent complex with a ligand of a tertiary phosphine or tertiary phosphite.

29. The production process as claimed in claim 27, wherein the palladium catalyst is a precursor complex capable of being readily converted into a low-valence complex in the reaction system.

30. The production process as claimed in claim 27, wherein the palladium catalyst is a low-valence complex with a ligand of tertiary phosphine and/or tertiary phosphite that is formed from a combination of a palladium complex not having a ligand of a tertiary phosphine or tertiary phosphite, and a tertiary phosphine and/or a tertiary phosphite in the reaction system.

31. A luminescent or electrochromic element that comprises a polymer having a 9-oxo-9-phosphafluorene-2,7-diyl skeleton of the following general formula [I]:

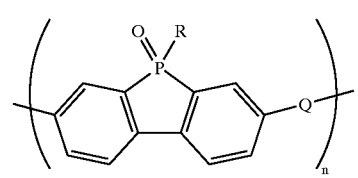

[I]

(wherein -Q-, R and n have the same meanings as above).

32. A process for producing a 2,7-dihalo-9-oxo-9-phosphaflorene compound of the following general formula [VI]:

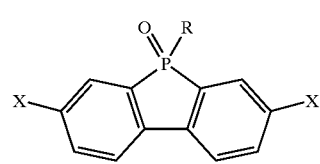

[VI]

(in which R has the same meaning as above; and X represents a halogen atom), which comprises halogenating a 9-oxo-9-phosphafluorene of the following general formula [IX]:

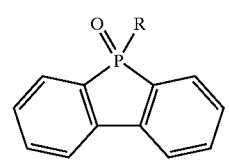

[IX]

(in which R represents a hydrogen atom, or an optionally-substituted alkyl, cycloalkyl, aralkyl, aryl, alkoxy, cycloalkyloxy, aralkyloxy or aryloxy group), with a halogen molecule.

33. The production process as claimed in claim 32, wherein the halogenation is effected in the presence of a Lewis acid catalyst.

34. The production process as claimed in claim 33, wherein the Lewis acid catalyst is a metal or a metal salt.
35. The production process as claimed in claim 34, wherein the metal to form the Lewis acid catalyst is iron, aluminium or antimony.
36. A 2,7-dihalo-9-oxo-9-phosphafluoene compound of the following general formula [VI]
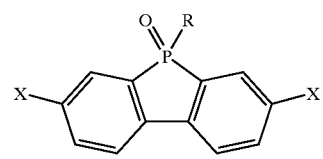
(wherein R and X have the same meanings as above).
* * * * *